United States Patent
Matsuda

(10) Patent No.: US 11,390,838 B2
(45) Date of Patent: Jul. 19, 2022

(54) SHAKING CULTURE APPARATUS AND CULTURE METHOD USING THE SAME

(71) Applicant: FUJIMORI KOGYO CO., LTD., Tokyo (JP)

(72) Inventor: Hiroyuki Matsuda, Tokyo (JP)

(73) Assignee: FUJIMORI KOGYO CO., LTD., Tokyo (JP)

( * ) Notice: Subject to any disclaimer, the term of this patent is extended or adjusted under 35 U.S.C. 154(b) by 237 days.

(21) Appl. No.: 15/540,024

(22) PCT Filed: Jan. 27, 2016

(86) PCT No.: PCT/IB2016/000051
§ 371 (c)(1),
(2) Date: Jun. 26, 2017

(87) PCT Pub. No.: WO2016/120708
PCT Pub. Date: Aug. 4, 2016

(65) Prior Publication Data
US 2018/0016534 A1    Jan. 18, 2018

(30) Foreign Application Priority Data

Jan. 29, 2015  (JP) .............................. JP2015-015426

(51) Int. Cl.
*C12M 3/06* (2006.01)
*C12M 1/00* (2006.01)
(Continued)

(52) U.S. Cl.
CPC .............. *C12M 27/16* (2013.01); *C12M 1/00* (2013.01); *C12M 1/02* (2013.01); *C12M 1/04* (2013.01);
(Continued)

(58) Field of Classification Search
CPC ....... C12M 23/14; C12M 27/10; C12M 27/16
See application file for complete search history.

(56) References Cited

U.S. PATENT DOCUMENTS

| 4,293,643 A | 10/1981 | Ohtake et al. |
| 4,673,297 A * | 6/1987 | Siczek ............... B01F 11/0014 |
| | | 366/208 |

(Continued)

FOREIGN PATENT DOCUMENTS

| EP | 0976448 A1 | 2/2000 |
| JP | S52-044286 A | 4/1977 |

(Continued)

OTHER PUBLICATIONS

Honda et al. "Production of Regenerated Plantlet Using Shaking Vessel-Type Bioreactor." Journal of Chemical Engineering of Japan, vol. 30 No. 1 1997, pp. 179-182. (Year: 1997).*

(Continued)

*Primary Examiner* — William H. Beisner
(74) *Attorney, Agent, or Firm* — Hauptman Ham, LLP

(57) ABSTRACT

The present invention provides a shake-type culture apparatus which can perform large scale culture without using stirring blades and a culture method using the same. More particularly, there are provided a shake-type culture apparatus comprising: a culture bag made from a soft packaging material; an outer shell container being arranged to house the entirety of the culture bag to be able to perform adjustment of a temperature thereof; and a power source for shaking the outer shell container housing the culture bag, wherein the contents in the culture bag can be stirred and mixed by shaking the outer shell container housing the culture bag; and a culture method using the same.

7 Claims, 3 Drawing Sheets

(51) Int. Cl.
    *C12N 1/00*      (2006.01)
    *C12M 1/04*      (2006.01)
    *C12M 1/02*      (2006.01)
    *C12M 1/34*      (2006.01)

(52) U.S. Cl.
    CPC ............ *C12M 23/14* (2013.01); *C12M 23/38* (2013.01); *C12M 29/00* (2013.01); *C12M 41/14* (2013.01); *C12M 41/26* (2013.01); *C12M 41/34* (2013.01); *C12N 1/00* (2013.01)

(56) References Cited

U.S. PATENT DOCUMENTS

| | | | | |
|---|---|---|---|---|
| 5,921,676 | A | * | 7/1999 | Reynolds ............ B01F 11/0028 366/208 |
| 9,260,698 | B2 | | 2/2016 | Antwiler |
| 9,273,278 | B2 | | 3/2016 | Lee et al. |
| 2004/0190372 | A1 | * | 9/2004 | Goodwin ............ B01F 13/0818 366/273 |
| 2006/0193198 | A1 | * | 8/2006 | Bae ..................... B01F 11/0014 366/111 |
| 2007/0269888 | A1 | | 11/2007 | Houtzager et al. |
| 2009/0180933 | A1 | | 7/2009 | Kauling et al. |
| 2009/0233334 | A1 | | 9/2009 | Hildinger et al. |
| 2010/0112700 | A1 | | 5/2010 | Shaaltiel et al. |
| 2011/0014689 | A1 | * | 1/2011 | Gandlur ............. B01F 11/0028 435/289.1 |
| 2013/0171616 | A1 | | 7/2013 | Niazi |

FOREIGN PATENT DOCUMENTS

| | | | | |
|---|---|---|---|---|
| JP | S55-102399 | A | | 8/1980 |
| JP | H04-126070 | A | | 4/1992 |
| JP | H04-158782 | A | | 6/1992 |
| JP | H05-146287 | A | | 6/1993 |
| JP | 7-155170 | A | | 6/1995 |
| JP | 10-150972 | A | | 6/1998 |
| JP | H10-314568 | A | | 12/1998 |
| JP | 2004-141847 | A | | 5/2004 |
| JP | 2005-261230 | A | | 9/2005 |
| JP | 2007-282629 | A | | 11/2007 |
| JP | 2008-513034 | A | | 5/2008 |
| JP | 2008-212049 | A | | 9/2008 |
| JP | 2009-534171 | A | | 9/2009 |
| JP | 2009-254340 | A | | 11/2009 |
| JP | 2010-525833 | A | | 7/2010 |
| JP | 2011-152076 | A | | 8/2011 |
| JP | 2012-120495 | A | | 6/2012 |
| JP | 4986659 | B2 | | 7/2012 |
| JP | 5214714 | B2 | | 6/2013 |
| JP | 2013-176377 | A | | 9/2013 |
| JP | 2014-158461 | A | | 9/2014 |
| KR | 10-2009-0017530 | A | | 2/2009 |
| WO | WO-0004131 | A1 | * | 1/2000 ............... A61J 1/05 |
| WO | 2007/121958 | A1 | | 11/2007 |
| WO | WO-2013040161 | A1 | * | 3/2013 ............. B01F 7/162 |
| WO | 2013/148511 | A1 | | 10/2013 |
| WO | 2014/093444 | A1 | | 6/2014 |

OTHER PUBLICATIONS

Klockner et al. "Advances in shaking technologies." Trends in Biotechnology Jun. 2012, vol. 30, No. 6, pp. 307-314. (Year: 2012).*
Liu et al. "Development of a shaking bioreactor system for animal cell cultures." Biochemical Engineering Journal 7 (2001) 121-125. (Year: 2001).*
Stettler et al. "Novel Orbital Shake Bioreactors for Transient Production of CHO Derived IgGs." Biotechnol. Prog. 2007, 23, 1340-1346. (Year: 2007).*
Notice of Allowance for Japanese Patent Application No. 2015-015426 dated May 8, 2018 and English machine translation thereof, 5 pp.
International Search Report in PCT/IB2016/000051, dated Apr. 5, 2016.
Reclari et al., "Surface wave dynamics in orbital shaken cylindrical containers", AIP Physics of Fluids, vol. 26, No. 5, May 8, 2014, pp. 1-11.
Extended European Search Report for European Patent Application No. 16742842.4, dated Aug. 22, 2018, 9 pages.
Office Action for Korean Patent Application No. 10-2017-7017498 with English translation, dated Sep. 17, 2018, 9 pages.
Japanese Office Action for Japanese Application No. 2015-015426, dated Nov. 14, 2017, 9 pages.
Written Opinion of the International Searching Authority, dated Apr. 5, 2016 for PCT/IB2016/000051, 23 pages.
Japanese Office Action for Japanese Application No. 2015-015426, dated Apr. 27, 2017, 13 pages.
Office Action for Chinese Patent Application No. 201680004525.X dated Dec. 28, 2018 and English translation thereof; 13 pages.
Office Action for Korean Patent Application No. 10-2017-7017498 dated Mar. 27, 2019 and English translation thereof; 6 pages.
Office Action for Japanese Patent Application No. 2018-102725 dated Apr. 2, 2019 and English translation thereof; 8 pages.
Notice of Allowance for Korean Patent Application No. 10-2017-7017498 dated Nov. 26, 2019 and English summary thereof; 2 pgs.
Notice of Allowance for Japanese Patent Application No. 2018-102725 dated Nov. 5, 2019 and English summary thereof; 5 pgs.
Office Action for Chinese Patent Application No. 201680004525.X dated Jul. 22, 2019 and English summary thereof; 10 pgs.
Office Action for Taiwanese Patent Application No. 105102307 dated Aug. 29, 2019 and English summary thereof; 10 pgs.
Office Action for Korean Patent Application No. 10-2017-7017498 dated Sep. 26, 2019 and English translation thereof; 6 pgs.
Office Action for Chinese Patent Application No. 201680004525.X dated May 9, 2019 and English summary thereof; 9 pgs.
Office Action for Taiwanese Patent Application No. 105102307 dated Feb. 4, 2020 and English summary thereof; 7 pages.
Notice of Allowance for Taiwanese Patent Application No. 105102307 dated May 4, 2020 and English summary thereof; 3 pgs.
Office Action for Indian Patent Application No. 201717022250; dated Sep. 29, 2020; 7 pgs.
Office Action in corresponding Chinese Patent Application No. 201680004525.X dated Sep. 8, 2021 with English summary; 9 pgs.
Decision of Appeal for Chinese Patent Application No. 201680004525.X dated Jan. 30, 2022; 12 pgs.

* cited by examiner

SHAKING CULTURE APPARATUS AND CULTURE METHOD USING THE SAME

CROSS REFERENCE TO RELATED APPLICATION

This application is a 371 of PCT/IB2016/000051 filed on Jan. 27, 2016, which, in turn, claimed the priority of Japanese Patent Application No. 2015-015426 which was filed on Jan. 29, 2015, the content of which is incorporated herein by reference.

TECHNICAL FIELD

The present invention relates to a shake-type culture apparatus and a culture method using the same.

BACKGROUND TECHNOLOGY

Large-scale culture of microorganisms, insect cells, plant cells, animal cells, and the like is widely used for producing medicines, foods, and cosmetics, as well as various substances useful as raw materials thereof and the like.

Patent Document 1 describes a culture bag airtightly housing a stirring device provided with a rotating shaft having stirring blades. In this culture apparatus, the considerably high shear (shearing stress) due to the stirring blades was generated in the system upon stirring. Additionally, there was generation of particles due to gliding of a bearing portion of the stirring blades. Furthermore, there were the problem of the cost, and the problem of a method of connecting the stirring blades and the culture bag.

Patent Document 2 describes a culture apparatus in which a culture bag composed of a flat bag is fixed in a tray-like supporting device. In the case of this culture apparatus, since the flat bag is arranged horizontally, there was the problem that an occupation area is increased upon scale up.

DOCUMENTS OF RELATED ART

Patent Documents

Patent Document 1: Japanese Patent No. 4986659
Patent Document 2: Japanese Patent No. 5214714

SUMMARY OF THE INVENTION

Problem to be Solved by the Invention

The present invention has been made in view of the above-mentioned circumstances, and an object thereof is to provide a shake-type culture apparatus which can perform large scale culture without using stirring blades and a culture method using the same.

Means for Solving the Problem

In order to solve the above-mentioned problems, the present invention provides a shake-type culture apparatus comprising: a culture bag made from a soft packaging material; an outer shell container being arranged to house the entirety of the culture bag to be able to perform adjustment of a temperature thereof; and a power source for shaking the outer shell container housing the culture bag, wherein contents in the culture bag can be stirred and mixed by shaking the outer shell container housing the culture bag.

It is preferable that the outer shell container housing the culture bag rotates in a horizontal direction.

It is preferable that the outer shell container housing the culture bag has a rotation number of shaking of 0.1 to 2,000 rpm and an amplitude of 0.1 to 100 mm.

It is preferable that the culture apparatus comprises a detector 28 for detecting a height of a wave of the contents in the culture bag, and is provided with an adjustment mechanism for adjusting the rotation number of shaking of the outer shell container housing the culture bag so that the height of the wave of the contents becomes constant.

It is preferable that the outer shell container comprises a jacket structure through which circulating water can be passed or a rubber heater.

It is preferable that the culture bag is a gusset bag, and is provided with a spout.

It is preferable that the culture apparatus is provided with a sensor for measuring a pH or a dissolved oxygen concentration (DO) of the contents in the culture bag, and a feedback control mechanism based on data obtained by the sensor.

It is preferable that the culture bag is provided with an injection port for pouring an acid or an alkali to make a pH of the contents constant.

It is preferable that the culture bag can be connected to each tube for adding and taking out the contents.

It is preferable that the culture bag is provided with a mechanism for supplying air or oxygen to the contents.

It is preferable that an internal space of the outer shell container has a cylindrical shape, a circle of a cylinder is positioned on a bottom face of an outer shell, and a ratio of a diameter of the circle and a height of the cylinder is 1:2 to 2:1.

It is preferable that the contents are housed in the culture bag, and the culture bag is deformed due to the weight of the contents, to be attached firmly to an internal surface of the outer shell container, so that the culture bag is supported by the outer shell container.

Also, the present invention provides a culture method using the shake-type culture apparatus.

Effects of Invention

According to the present invention, by using the outer shell container and not using the stirring blades, scale up from a small volume to a large volume is easy. Additionally, by shaking the container, a small volume to a large volume can be stirred in one container with the low shear (shearing stress), and effective cell culture can be performed. Additionally, since the culture apparatus has no stirring blades, generation of particles due to a bearing portion of the stirring blades can be suppressed. Even when the apparatus is contaminated by culture, since it is enough to exchange the culture bag, and it is not necessary to dispose the stirring blades and the stirring magnet, the culture apparatus which is less expensive than before can be provided.

BEST MODE FOR CARRYING OUT THE INVENTION

Figure 1:
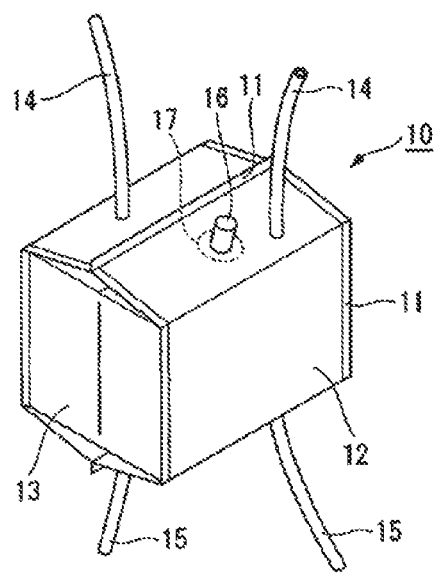
FIG. 1 is a perspective view showing one example of a culture bag.

Referring to the drawings, the present invention will be illustrated below based on preferable embodiments.

FIG. 1 shows one example of a culture bag 10. This culture bag 10 is composed of a soft packaging material such as films 12, 13. FIG. 1 shows a gusset bag which is sealed by arranging one pair of films 13 with a gusset between one pair of films 12, and providing a sealing portion 11 at the peripheral edge of the films 12, 13. Examples of a shape of the bag include a cylindrical type, a square cylindrical type, and the like. When the culture bag 10 is a multiple packaging bag such as a double bag and a triple bag, since the liquid is hardly leaked, this is more preferable.

A material of the films constituting the culture bag 10 is not particularly limited, but includes thermoplastic resins such as a polystyrene, a polyamide, a polyester, and a polyolefin, or a laminate thereof. It is preferable that the film used in the culture bag 10 is the same material as that of the film used in a purification step. By using the same material in a culturing step and a purification step, it becomes easy to secure product quality of the prepared medicines.

The volume (size) of the culture bag 10 is not particularly limited, but can be, for example, the size of 0.1 L to 5,000 L and preferably 1 to 2,000 L. The culture bag 10 may be single use (disposable).

For the purpose of addition, taking out, or the like of the contents such as a culture medium and the atmospheric gas, a plurality of tubes 14, 15 can be connected to the culture bag 10. Additionally, the culture bag 10 can be provided with a spout 16. A cock, a cap, a taper-shaped pouring port, or the like can also be provided in the spout 16. Tubes 14, 15 may also be connected to the spout 16. In the case of the present embodiment, by sealing a base 17 of the spout 16 on a back side of the film 12, the spout 16 is fixed to the culture bag 10.

A material of the tube is not particularly limited, but a material excellent in chemical resistance, weather resistance, and the like such as silicone and a thermoplastic elastomer is preferable. In the tube, a filter, a flow monitor, a flowmeter, a valve, a pump, and the like may be provided. It is preferable that the culture bag 10 and the tubes 14, 15 have been sterilized before culturing. A sterilizing means can be appropriately selected depending on the culturing purpose or the like, and specific examples thereof include radiation such as γ-ray; the gas such as ethylene oxide; heating with the water vapor or the like; and the like.

Figure 2:
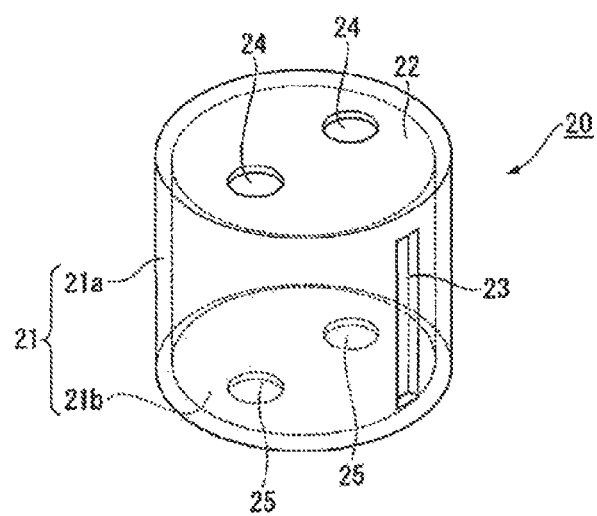
FIG. 2 is a perspective view showing one example of an outer shell container.
Figure 3:
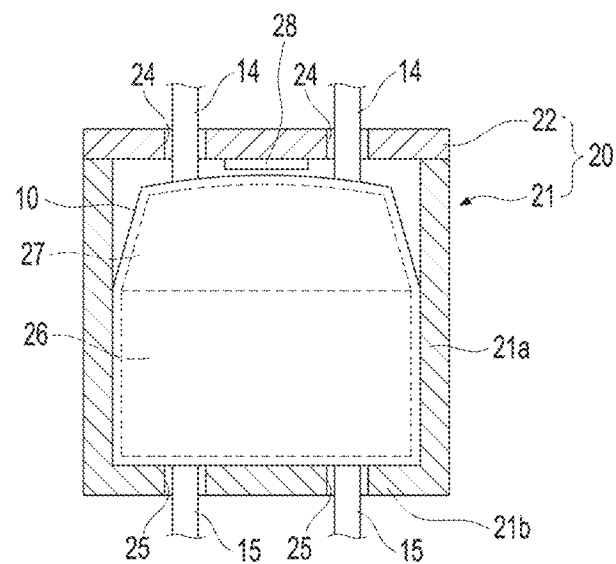
FIG. 3 is a cross-sectional view showing one example of an outer shell container housing a culture bag.

FIG. 2 shows one example of an outer shell container 20. Additionally, FIG. 3 shows a cross-sectional view of the state where the culture bag 10 of FIG. 1 is housed in the outer shell container 20 of FIG. 2. To protect the culture bag 10 composed of a soft packaging material, the outer shell container 20 can house the entirety of the culture bag 10 as shown in FIG. 3.

A configuration of the outer shell container is not particularly limited, and the outer shell container 20 as shown in FIG. 2 is provided with a container body 21 having a side wall portion 21a and a bottom wall portion 21b, and a lid portion 22 for closing an upper opening of the side wall portion 21a. When the entirety or the majority can be housed by the side wall portion 21a in a vertical direction of the culture bag 10, the lid portion 22 may be omitted. A lower portion of a side face of the culture bag 10 can also be covered with the container body 21, and an upper portion of a side face of the culture bag 10 can also be covered with the lid portion 22.

In order to suppress temperature variation of the interior, it is preferable that an opening of the outer shell container 20 for taking in and out the culture bag 10 is closed with the lid portion 22. The lid portion 22 may be of the detaching type so that it can be separated from the container body 21, or may be openably/closably connected to the container body 21 with a hinge or the like.

It is preferable that a material of the outer shell container 20 (for example, a container body 21 and a lid portion 22) has such hardness (rigidity) that the culture bag 10 can be protected, and examples thereof include a metal such as stainless, a resin, a timber, a glued laminated timber, a composite material such as a fiber-reinforced plastic.

It is preferable from a view point of the stirring efficiency that an internal space of the outer shell container has a cylindrical shape, and a circular portion of a cylinder is positioned on a bottom face of the outer shell container. The ratio of a diameter (internal diameter) of a circle positioned on a bottom face of a cylinder of an internal space and the height of a cylinder is, for example, 1:2 to 2:1. The internal diameter and the height may be equal (ratio is 1:1).

It is preferable that the contents of the culture bag 10 housed in the outer shell container 20 contain the liquid (culture medium) 26 and the gas 27. The volumetric ratio of the gas and the liquid (gas-liquid volumetric ratio) is not particularly limited, and the liquid may be more than the gas, or the gas may be more than the liquid, or both may be in approximately equal amounts. The gas-liquid volumetric ratio is preferably, for example, in the range of 1:9 to 9:1. It is preferable that in the entirety or the majority of the range that the culture bag 10 houses at least the liquid (culture medium) 26, the culture bag 10 is firmly attached to the outer shell container 20, and the outer shell container 20 supports a side face of the culture bag 10. At a portion at which the gas 27 is housed in the culture bag 10, an upper portion (a part) of the culture bag 10 may be exposed above (outside) the outer shell container 20.

The culture medium 26 is not particularly limited as far as it can be stirred by shaking, and may be a solution, an emulsion, a suspension, a dispersion, a gel or the like. The culture medium 26 may be a uniform monophasic composition, or may be composed of two or more phases, for example, the liquid containing the solid matter, and the like. It is preferable that the culture medium 26 has been sterilized before culturing. Furthermore, the culture medium 26 can contain living bodies (culturing subject) such as microorganisms, insect cells, plant cells, animal cells, tissues, cell sheets, and cell masses. In culture requiring a scaffold, the solid matter such as a particle, a mass, an expanded body, and a fiber may also be mixed into a culture medium as a culture substrate.

The gas 27 may be an aerobic atmosphere containing the air (or $O_2$-containing gas), or may be an anaerobic atmosphere having the low $O_2$ concentration. The composition of the gas 27 is not particularly limited, but is generally a mixed gas of two or more gases. Examples of a component of the gas 27 include an oxidative gas such as oxygen ($O_2$); an inert gas such as nitrogen ($N_2$) and argon (Ar); an acidic gas such as carbon dioxide ($CO_2$); a basic gas such as ammonia ($NH_3$); a reducing gas such as hydrogen sulfide ($H_2S$); and the like. As the gas to be supplied to the culture bag 10, the gas which has been passed through a filter is preferable. It is preferable that the gas such as the air, oxygen, and carbon dioxide is introduced from any one or both of a lower side (liquid side) or upper side (gas side).

The side wall portion 21a has a window 23 for visually confirming an amount of the contents (liquid surface) of the culture bag 10 housed in the outer shell container 20. The window 23 is provided as a slit-like notch in a vertical direction of the side wall portion 21a. The window 23 may be opened, or may be closed with a transparent material. Additionally, the bottom wall portion 21b and the lid portion 22 have holes 24, 25 through which tubes 14, 15 are passed.

In the present embodiment, there were two tubes 14 on an upper surface of the culture bag 10 and two tubes 15 on a lower surface of the culture bag 10, but arrangement and the number of tubes 14, 15 are not particularly limited, and the desired number of tubes can be provided at appropriate positions. Tubes can be arranged, for example, at any one or two or more of an upper portion, a lower portion, and a side portion of the culture bag. Through these tubes, sampling of the contents, introduction and discharge of the fluid (gas, liquid, powder, and the like), supply of nutrients, removal of waste products, and the like can be performed. A configuration is also possible that, through tubes, a circulation pathway including the culture bag and an external device is provided, and after a part of the culture liquid is treated with the external device, it is returned to the culture bag.

When the culture bag 10 is housed in the outer shell container 20 as shown in FIG. 3, the culture bag 10 is deformed according to the weight of the contents, and is firmly attached to an internal surface of the outer shell container 20. By contact between the culture bag 10 and the outer shell container 20 over a wide area, they are firmly attached even without mechanical fitting or engaging, or chemical adhesion or adsorption, and a fixing force enduring shaking is generated. It is preferable that an internal surface of the outer shell container 20 is smooth, and has been polished, for example, by puffing or the like. There may be mild irregularity on an internal surface, but it is preferable that the culture bag does not have such fine irregularity and shape change (acute angle or the like) that damage and deterioration of films 12, 13 are caused to the thickness of films 12, 13 constituting the culture bag 10 (see FIG. 1).

It is preferable that the outer shell container 20 has a temperature adjusting mechanism (means) so that temperature adjustment of the culture bag 10 and the contents thereof can be performed. Examples of the temperature adjusting mechanism include, but are not limited to, a jacket structure through which a heat medium such as circulating water can be passed; a heating device such as a rubber heater; and the like.

Figure 4:
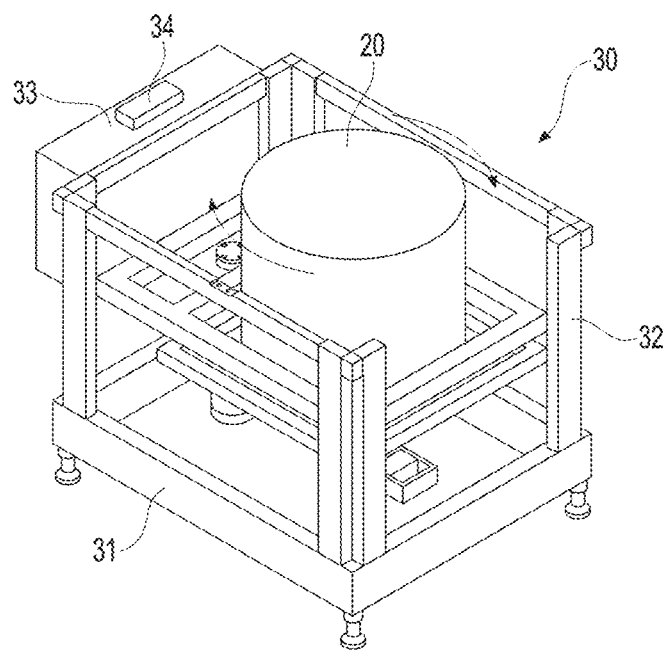
FIG. 4 is a perspective view showing one example of a shake-type culture apparatus.

FIG. 4 shows one example of a shaking device 30 which shakes the outer shell container 20. The shaking device 30 comprises a base portion 31 and a frame portion 32 surrounding the outer shell container 20, and a power source 33 which shakes the outer shell container 20. The shaking device 30 can shake the outer shell container 20 while the culture bag 10 is housed, as shown in FIG. 3. The shake-type culture apparatus of the present embodiment is provided with the outer shell container 20 housing the culture bag 10, and the shaking device 30, and can perform culture while the contents in the culture bag 10 are stirred and mixed by shaking the outer shell container 20 housing the culture bag 10.

Figure 5A:
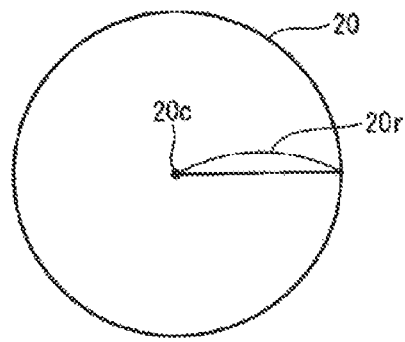
FIG. 5A is a plan view showing one example of an outer shell container.
Figure 5B:
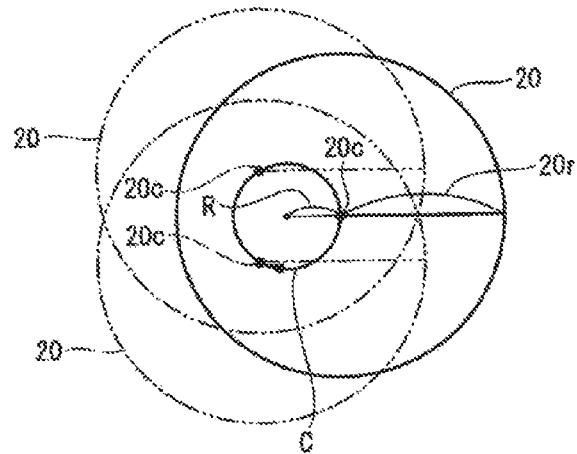
FIG. 5B is a plan view showing one example of a shaking movement of an outer shell container.

FIG. 5B shows one example of a shaking action of the outer shell container. In the present embodiment, a planar shape of the outer shell container 20 is a circular shape, and a three-dimensional shape thereof is a cylinder with a central axis being toward approximately vertical. FIG. 5A shows a center 20c and a radius 20r of the outer shell container 20. In the shaking action of FIG. 5B, the center 20c of the outer shell container 20 rotates (revolves in orbit) on an orbit C of a radius R. In this case, the amplitude of shaking is two times of the radius R. Further, the outer shell container 20 may rotate (turn on its axis) around the center 20c. The radius R of an illustrated example is smaller than the radius 20r, but the illustrated ratio does not particularly represent the actual ratio precisely.

It is preferable that upon shaking, the outer shell container 20 housing the culture bag 10 rotates in a horizontal direction. A rotation direction may include both a horizontal component and a vertical component. It is preferable that the magnitude of the vertical component is smaller than the magnitude of the horizontal component (including the case where the vertical component is 0). Not by shaking in one direction, but by incorporating rotation, effective stirring can be performed. The shear (shearing stress) at stirring is hardly applied to the culture bag, and effective culture can be attained. A speed and a direction of rotation can be appropriately controlled. By changing the rotation speed and the rotation direction, not only stirring of the liquid in a horizontal direction, but also stirring in a vertical direction can be realized.

It is preferable that the rotation number, the amplitude, and the like are set depending on the system of culture, and are controlled by a program. For example, in culture of *Escherichia coli*, it is preferable that culture is performed by increasing the dissolved oxygen concentration (DO) in a solution. To increase the DO, it is preferable to perform vigorous shaking to intensify mixing of the gas and the liquid. Meanwhile, in culture of animal cells, it is preferable to suppress foaming of the culture liquid and perform mild stirring. The shake-type culture apparatus of the present embodiment can perform culture, for example, by controlling one or two or more of the following control factors.

Rotation number and shaking direction of shaking of device

PH of culture medium

Airflow quantity of culture medium

Temperature of culture medium

Height of liquid level (height of wave)

Regarding a shaking direction, it is preferable that right rotation and left rotation, or forward rotation and reverse rotation are repeated at an arbitrary pattern. It is preferable to construct a system so that the rotational speed and the rotation number of the shaking device can be controlled with a control panel 34 or the like. It is preferable that, in the shaking device, a rotation direction can be arbitrarily switched. For this reason, it is preferable that a power source and a rotating device include a mechanism which can perform rotation in both forward and reverse directions. Additionally, it is preferable to control a rotation pattern, for example, by a program. The rotation pattern is not particularly limited, but examples include the following several examples.

(1) Forward rotation→stoppage→reverse rotation→stoppage→forward rotation→stoppage→reverse rotation→(repetition)

(2) Forward rotation→stoppage→forward rotation→stoppage→reverse rotation→stoppage→reverse rotation→(repetition)

(3) Forward rotation→stoppage→forward rotation→stoppage→forward rotation→stoppage→forward rotation→(repetition)

The rotation number and the amplitude of shaking of the outer shell container can be arbitrarily set, and it is preferable to detect the height of a wave, and adjust the rotation number from the height of a wave by feedback control or the like, in order that, when rotated, an increase width of the height of a wave of the contents in the culture bag (for example, average height of liquid level, maximum height, height difference, and the like) is within a certain range. The rotation number is preferably 0.1 to 2,000 rpm (rotation per minute), more preferably 0.1 to 200 rpm, further preferably 0.1 to 100 rpm, and most preferably 10 to 80 rpm. The amplitude is preferably 0.1 to 100 mm, more preferably 2 to 100 mm, and further preferably 10 to 30 mm. In addition, when a rotation direction is changed, the rotation number is the total of the rotation numbers (non-negative value) not depending on a rotation direction, such as a sum of the right rotation number and the left rotation number, or a sum of the forward rotation number and the reverse rotation number.

It is preferable that the culture bag is provided with a sensor for measuring a pH or DO of the contents, and a feedback control mechanism by data obtained by the sensor.

Concerning the hydrogen ion exponent (pH), a pH in the system can be known by inserting a pH electrode into the culture bag, or sticking a chip of which the color changes by a pH, in the system. When the system is desired to be acidic, a pH can be changed to an acidic side by introducing a $CO_2$ gas, or adding an acid solution dropwise. When a $CO_2$ gas is introduced, it is preferable to introduce a $CO_2$ gas from an upper surface of the culture bag, or intermittently introduce the gas from a bottom portion of the culture bag, in order to prevent a $CO_2$ gas from being dissolved in a solution more than necessary. When the system is desired to be basic, a pH can be made to be basic by adding an alkali solution. A port for placing an acid or an alkali for making a pH constant may be tubes 14, 15 or a spout 16, or may be provided at another place.

Concerning DO (dissolved oxygen concentration), it is preferable to measure an airflow quantity, perform feedback control, and introduce oxygen. As a method of supplying oxygen ($O_2$), it is preferable to introduce oxygen through a tube having an outlet in a solution (under liquid level) to diffuse oxygen in the solution.

Concerning a temperature of the contents (culture medium), temperature adjustment can be performed using the temperature adjusting mechanism (as described above) of the outer shell container 20. A culture temperature depends on a kind of an organism to be cultured and, for example, in the case of microorganisms, is preferably 4 to 40° C. and particularly preferably 25 to 37° C. When used as a device of stirring a culture medium or the like without culture, the contents may be cooled (for example, 4 to 20° C.). For managing a temperature, feedback control can be performed by incorporating a thermometer into the culture bag 10 and utilizing a measured value thereof. The thermometer may be a contact thermometer, but a stationary non-contact thermometer is preferable.

The shake-type culture apparatus of the present embodiment can be applied to both of feeding culture (fed-batch system) and perfusion culture (perfusion system). An organism, a cell or the like to be cultured is not particularly limited, and the culture apparatus can be used for culturing bacteria including *Escherichia coli*, yeast, microorganisms, insect cells, plant cells, animal cells, CHO (Chinese Hamster Ovary) cells for producing biomedicines, HeLa cells, COS cells, iPS cells for use in regenerative therapy, stem cells including mesenchymal stem cells, animal cells such as differentiated tissue cells, and the like. Among them, the culture apparatus is suitable for culturing CHO cells.

The shake-type culture apparatus of the present embodiment and a culture method using the same are particularly suitable for a large-scale culture. It is preferable that the shaking device is loaded with a counter balance, particularly in the case of large scale. When the counter balance is loaded, the apparatus can be stably operated even using the culture bag containing a large volume of a culture medium. By loading one shaking device with two or more culture bags, they may mutually function as the counter balance.

The present invention has been illustrated above based on suitable embodiments, but the present invention is not limited to the above-mentioned embodiments, and can be variously modified in a range not departing from the gist of the present invention.

The above-mentioned shaking device can also be utilized in stirring, preparation, a chemical reaction, fermentation, or the like of a composition (culture medium and the like), in addition to culture.

What is claimed is:

1. A shaking culture apparatus comprising:
   a culture bag made from a packaging material;
   an outer shell container being arranged to house the entirety of said culture bag to be able to perform adjustment of a temperature thereof;
   a shaking device comprising a base portion and a frame portion surrounding the outer shell container, and a power source for shaking said outer shell container housing said culture bag;
   a detector configured to detect a height of a wave of contents of the culture bag; and
   a control panel for adjusting a rotation number of shaking of said outer shell container housing said culture bag so that the height of the wave of the contents becomes constant,
   wherein said outer shell container is provided with a container body having a side wall portion and a bottom wall portion, and a lid portion for closing an upper opening of the side wall portion, the side wall portion has a window which is provided as a slit notch in a vertical direction, the bottom wall portion and the lid portion have holes through which tubes are passed,
   an internal space of said outer shell container has a cylindrical shape, a circle of a cylinder is positioned on a bottom face of said outer shell container, and a ratio of a diameter of the circle and a height of the cylinder is 1:2 to 2:1,
   said culture bag is a gusset bag of a square box shape which is sealed by arranging one pair of films with a gusset between another pair of films and providing a sealing portion at peripheral edges of both of the pair of films,
   said culture bag is provided with a spout which is fixed to the culture bag by sealing a base of the spout on a back side of one of the pair of films or one of the another pair of films,
   said tubes are provided on an upper surface and a lower surface of said culture bag respectively and each tube is passed through said holes of the bottom wall portion and the lid portion,
   contents containing liquid and gas are housed in said culture bag, a volumetric ratio of the liquid and the gas is 1:9 to 9:1, and said culture bag is firmly attached to said outer shell container in the range that said culture bag houses the liquid so that said culture bag is supported by said outer shell container, said contents in said culture bag can be stirred and mixed by shaking said outer shell container housing said culture bag, a center of the outer shell container rotates on an orbit of a circular shape, a rotation direction includes both a horizontal component and a vertical component, and a magnitude of the vertical component is smaller than a magnitude of the horizontal component provided that the magnitude of the vertical component is not 0, said outer shell container housing said culture bag has a rotation number of shaking of 10 to 80 rpm and an amplitude of 10 to 30 mm, the shaking device is loaded with a counter balance, and wherein the control panel is configured to change a rotation speed and a rotation direction of said shaking device, based on the detected height of the wave, not only stirring of the liquid in a horizontal direction, but also stirring in a vertical direction are realized.

2. The shaking culture apparatus according to claim 1, wherein said outer shell container comprises a jacket structure through which circulating water can be passed or a rubber heater.

3. The shaking culture apparatus according to claim 1, wherein the shaking culture apparatus is provided with a sensor for measuring a pH or a dissolved oxygen concentration (DO) of the contents in said culture bag.

4. The shaking culture apparatus according to claim 1, wherein said culture bag is provided with an injection port for pouring an acid or an alkali to make a pH of said contents constant.

5. The shaking culture apparatus according to claim 1, wherein said culture bag is connected to each tube for adding and taking out said contents.

6. The shaking culture apparatus according to claim 1, wherein said culture bag is provided with a tube for supplying air or oxygen to said contents.

7. A culture method comprising a step of culturing an organism or a cell by using the shaking culture apparatus according to claim 1.

* * * * *